United States Patent
Lortscher

(10) Patent No.: US 10,064,884 B2
(45) Date of Patent: Sep. 4, 2018

(54) COMPOSITION AND METHODS OF TREATING ACNE AND PHOTOAGING

(71) Applicant: Curology, Inc., San Diego, CA (US)

(72) Inventor: David Lortscher, San Diego, CA (US)

(73) Assignee: Curology, Inc., San Diego, CA (US)

( * ) Notice: Subject to any disclaimer, the term of this patent is extended or adjusted under 35 U.S.C. 154(b) by 0 days.

(21) Appl. No.: 15/223,229

(22) Filed: Jul. 29, 2016

(65) Prior Publication Data

US 2017/0049795 A1 Feb. 23, 2017

Related U.S. Application Data

(60) Provisional application No. 62/199,092, filed on Jul. 30, 2015.

(51) Int. Cl.
| | |
|---|---|
| *A01N 43/04* | (2006.01) |
| *A61K 31/70* | (2006.01) |
| *A61K 31/7056* | (2006.01) |
| *A61K 31/194* | (2006.01) |
| *A61K 31/203* | (2006.01) |
| *A61K 31/315* | (2006.01) |
| *A61K 31/4406* | (2006.01) |
| *A61K 31/7048* | (2006.01) |
| *A61K 8/36* | (2006.01) |
| *A61K 8/362* | (2006.01) |
| *A61K 8/49* | (2006.01) |
| *A61K 8/55* | (2006.01) |
| *A61K 8/58* | (2006.01) |
| *A61K 8/60* | (2006.01) |
| *A61K 9/00* | (2006.01) |
| *A61K 31/20* | (2006.01) |
| *A61K 31/455* | (2006.01) |
| *A61K 31/555* | (2006.01) |
| *A61K 31/665* | (2006.01) |
| *A61Q 19/08* | (2006.01) |
| *A61K 31/7028* | (2006.01) |
| *A61K 31/7042* | (2006.01) |
| *A61K 31/7052* | (2006.01) |

(52) U.S. Cl.
CPC .......... *A61K 31/7056* (2013.01); *A61K 8/361* (2013.01); *A61K 8/362* (2013.01); *A61K 8/4926* (2013.01); *A61K 8/55* (2013.01); *A61K 8/58* (2013.01); *A61K 8/602* (2013.01); *A61K 9/0014* (2013.01); *A61K 31/194* (2013.01); *A61K 31/20* (2013.01); *A61K 31/203* (2013.01); *A61K 31/315* (2013.01); *A61K 31/4406* (2013.01); *A61K 31/455* (2013.01); *A61K 31/555* (2013.01); *A61K 31/665* (2013.01); *A61K 31/7048* (2013.01); *A61Q 19/08* (2013.01); *A61K 31/7028* (2013.01); *A61K 31/7042* (2013.01); *A61K 31/7052* (2013.01); *A61K 2800/59* (2013.01)

(58) Field of Classification Search
None
See application file for complete search history.

(56) References Cited

U.S. PATENT DOCUMENTS

| | | | |
|---|---|---|---|
| 2005/0169948 A1 | 8/2005 | Bernstein | |
| 2008/0069779 A1 | 3/2008 | Tamarkin et al. | |
| 2009/0246156 A1* | 10/2009 | Kunin | A61K 8/35 424/60 |
| 2010/0105638 A1* | 4/2010 | Den-Braven | A61K 8/67 514/99 |
| 2011/0256237 A1 | 10/2011 | Bernstein | |

FOREIGN PATENT DOCUMENTS

| | | |
|---|---|---|
| CN | 105287261 A | 2/2016 |
| EP | 0443413 A1 | 8/1991 |
| WO | 2007082780 A1 | 7/2007 |
| WO | 2010080543 A1 | 7/2010 |

OTHER PUBLICATIONS

Leyden J. Am. Acad. Dermatol. (2003), vol. 49, No. 3, S200-S210.*
Gollnick et al. (Jan. 1, 1998) "Topical Drug Treatment in Acne," Dermatology. 196(1):119-125.
Pazoki-Toroudi et al. (Dec. 2011) "Combination of azelaic acid 5% and clindamycin 2% for the treatment of acne vulgaris," Cutaneous and Ocular Toxicology. 30(4):286-291.
Sardesai et al. (Mar. 2003) "Comparison of efficacy of topical clindamycin and nicotinamide combination with plain clindamycin for the treatment of acne vulgaris and acne resistant to topical antibiotics," Indian Journal of Dermatology, Venereology, and Leprology. 69(2):138-139.
Webster (Jan. 1, 2000) "Combination azelaic acid therapy for acne vulgaris," Journal of the American Academy of Dermatology. 43(2):S47-S50.
International Search Report corresponding to International Patent Application No. PCT/US2016/044679, dated May 3, 2017.

* cited by examiner

*Primary Examiner* — Patrick T Lewis
(74) *Attorney, Agent, or Firm* — Lathrop Gage L.L.P.

(57) ABSTRACT

Pharmaceutical compositions comprising a first anti-acne compound, a second anti-acne compound, and an anti-photoaging compound are described. Methods for the treatment of acne and photoaging using the compositions are also described.

24 Claims, 1 Drawing Sheet

|  |  | I  0.15% |  |  |
|  |  | H  0.09% |  | Q  0.14% |
|  |  | G  0.06% |  | P  0.07% |
|  |  | F  0.04% | L  0.1% | O  0.035% |
|  |  | E  0.018% | K  0.05% | N  0.02% |
| B  Zinc-Nia-Clinda | C  AzA-Clinda-Nia | D  0.009%  Tret*-AzA-Clinda | J  0.017%  Tret*-AzA-Zin | M  0.012%  Tret*-VitC-Nia |

COMPOSITION AND METHODS OF TREATING ACNE AND PHOTOAGING

RELATED APPLICATIONS

This application claims priority to U.S. Patent Application Ser. No. 62/199,092, titled "Compositions And Methods Of Treating Acne And Photoaging", filed Jul. 30, 2015, the disclosure of which is incorporated herein by reference in its entirety.

TECHNICAL FIELD

The present invention relates generally to the field of dermatology and more specifically to compositions and methods for the treatment of acne and photoaging.

BACKGROUND

Acne occurs in greater than 90% of the population at some point in their lives. Although it is primarily considered a disorder of the teenage years, many people (and especially females) suffer from acne during adulthood. Acne (also known as acne vulgaris) is a long-term skin condition that is caused by: 1) plugging of hair follicles by abnormally keratinized cells, 2) microbial colonization of the follicle, 3) inflammation, and 4) increased oil production associated with circulating hormones.

Photoaging occurs naturally as our skin is exposed to the sun's ultraviolet rays, and the first signs of photoaging (including fine wrinkles and hyperpigmentation) typically appear between the ages of 20 and 35. While sun protection is key to minimizing photoaging, there are also various topical treatments which have proven to be efficacious for treating and preventing photoaging.

The desire to treat acne commonly coexists with the desire to treat and/or prevent photoaging. While the application of multiple dermatologic products is an option currently employed by many patients, the existence of a single, efficacious, stable composition would offer benefits in convenience and adherence.

There are numerous difficulties in formulating a single, efficacious, stable composition to treat or prevent acne and photoaging.

First, the successful treatment of acne alone typically involves using two different agents with complementary mechanisms of action. The most common categories are comedolytics (which help keratinization and thus prevent clogged pores) and antimicrobials (which generally target the acne-causing bacterium *Propionibacterium acnes* or *P. acnes*). So, the successful treatment of acne and photoaging together would typically require three or more active ingredients, which may require different vehicles, different frequencies of application, and different methods of application.

A second difficulty inherent in creating a combined formulation is that many anti-acne ingredients inactivate other anti-acne ingredients. For example, benzoyl peroxide inactivates tretinoin, erythromycin, and hydroquinone; tretinoin inactivates erythromycin; and benzoyl peroxide can lead to oxidation of zinc pyrithione. There are likely to be many more similar interactions that are not yet described in the dermatology literature.

When it is desired to use anti-photoaging ingredients in addition to anti-acne ingredients, additional interactions arise. When a patient is using benzoyl peroxide (for acne) they should avoid using it at the same time as hydroquinone (used for short-term treatment of photoaging), as the combination can lead to staining of the skin. As another example, niacinamide (a vitamin B3 derivative that can be used as an anti-acne ingredient and as an anti-photoaging ingredient) should not be used with ascorbic acid (the naturally occurring form of vitamin C), as the former can inactivate the latter ingredient. In addition, many photoaging treatments cannot be used long-term because they contain steroids or a bleaching agent (hydroquinone) with potential undesirable side effects.

Thus, for patients receiving treatment for both acne and photoaging, their treatments typically do not come in the same formulation, and additionally, the patients are often instructed to use their individual formulations at different times of day, significantly decreasing the convenience of treatment.

An additional difficulty in formulating a once-daily composition for the treatment of acne and photoaging is that the majority of ingredients for each of these purposes are typically applied to the skin twice daily. These ingredients that are typically applied twice daily include clindamycin, azelaic acid, dapsone, adapalene, benzoyl peroxide, erythromycin, hydroquinone, niacinamide, ascorbic acid, magnesium ascorbyl phosphate, zinc pyrithione, and others. Even for treatment of acne alone, once-daily treatments are not yet the norm because of the potential inactivation of one anti-acne compound by another anti-acne compound and using two different agents with different mechanisms of action often requiring different formulations.

Finally, a method to treat both acne and photoaging would require a collection of active ingredients that are stable and efficacious in the same vehicle. In formulating a vehicle of inactive ingredients to use along with active ingredient(s), one must account for texture, color, scent, method of application, pH, water solubility, alcohol solubility, stability of the active ingredients, and the presence or absence of interactions between the active ingredient(s) and the inactive ingredients. Thus for acne and photoaging to both be treated with a single treatment is a significant advance over most current methodologies. A once-daily composition and method of treatment would be desirable because a once-daily composition increases patient adherence and lowers cost.

BRIEF DESCRIPTION OF THE FIGURES

FIG. 1 shows Table 2, Exemplary pharmaceutical compositions, Compositions B-Q.

SUMMARY

In one aspect, the current disclosure provides a composition comprising a first anti-acne compound, a second anti-acne compound, and an anti-photoaging compound.

According to one embodiment, the composition comprises a) a first anti-acne compound;

b) a second anti-acne compound, wherein each of the first and second anti-acne compounds are selected from the group consisting of azelaic acid, clindamycin, niacinamide, tretinoin, and zinc pyrithione, or a pharmaceutically acceptable salt thereof; and c) an anti-photoaging compound, wherein the anti-photoaging compound is selected from the group consisting of azelaic acid, niacinamide, and ascorbyl phosphate, or a pharmaceutically acceptable salt thereof, wherein the first anti-acne compound, the second anti-acne compound, and the anti-photoaging compound are three different compounds.

In another aspect, the current disclosure provides a method for the treatment of acne and photoaging in a subject in need thereof comprising administering to the skin of the subject a composition comprising
  a) a first anti-acne compound;
  b) a second anti-acne compound, wherein each of the first and second anti-acne compounds are selected from the group consisting of azelaic acid, clindamycin, niacinamide, tretinoin, and zinc pyrithione, or a pharmaceutically acceptable salt thereof; and
  c) an anti-photoaging compound, wherein the anti-photoaging compound is selected from the group consisting of azelaic acid, niacinamide, and ascorbyl phosphate, or a pharmaceutically acceptable salt thereof; and
  d) a pharmaceutically acceptable vehicle,
wherein the first anti-acne compound, the second anti-acne compound, and the anti-photoaging compound are three different compounds.

In yet another aspect, the current disclosure provides a method for the treatment of acne and photoaging in a subject in need thereof comprising
  a) administering to the skin of the subject a first composition, wherein the first composition comprises less than 0.025% tretinoin and less than 12% azelaic acid;
  b) evaluating the skin of the subject after a first interval; and
  c) administering a second composition comprising a higher concentration of tretinoin or azelaic acid or both than the first composition if the acne or photoaging requires further improvement,
  thereby treating acne and photoaging in the subject.

In still another aspect, the current disclosure provides a kit comprising:
  1) a composition comprising
    a) a first anti-acne compound;
    b) a second anti-acne compound, wherein each of the first and second anti-acne compounds are selected from the group consisting of azelaic acid, clindamycin, niacinamide, tretinoin, and zinc pyrithione, or a pharmaceutically acceptable salt thereof; and
    c) an anti-photoaging compound, wherein the anti-photoaging compound is selected from the group consisting of azelaic acid, niacinamide, and ascorbyl phosphate, or a pharmaceutically acceptable salt thereof,
    wherein the first anti-acne compound, the second anti-acne compound, and the anti-photoaging compound are three different compounds;
  2) a sealed container for housing the composition; and
  3) instructions for use.

DETAILED DESCRIPTION

The disclosure provides a pharmaceutical composition for the treatment of skin disorders. According to some embodiments, the pharmaceutical composition is a topically administered composition. According to some embodiments, the pharmaceutical composition comprises three distinct pharmaceutical ingredients. According to some embodiments, each of the three distinct pharmaceutical ingredients are supplied in a single topical pharmaceutical composition. According to some embodiments, the single topical pharmaceutical composition is administered to the skin of a subject in need thereof once a day.

The disclosure also provides methods of administering a pharmaceutical composition with three distinct pharmaceutical ingredients supplied in a single topical pharmaceutical composition to a subject in need thereof. According to some embodiments, the subject is suffering from a skin pathology. According to some embodiments, the skin pathology is selected from acne, wrinkles, photoaging and uneven pigmentation. According to some embodiments, administration of the topical pharmaceutical composition to the skin of a subject results in reduction of fine lines and wrinkles, reduction in acne, reduction of the appearance of fine lines and wrinkles, skin firming, improvement in skin texture, improvement in the skin's elasticity, improvement in skin luminosity, reduction of uneven pigmentation, skin hydration, skin moisturization, reduction in skin dehydration, and improvement of even skin tone.

According to some embodiments, the method includes evaluating the skin of a subject. According to some embodiments, the method includes the evaluation of the skin of a subject using telemedicine. According to some embodiments, the subject is administered a first topical pharmaceutical composition. According to some embodiments, the skin of the subject is reevaluated. According to some embodiments, if the skin evaluated has not improved, a second topical pharmaceutical composition is administered. According to some embodiments, the second topical pharmaceutical composition comprises ingredients that cause enhanced skin irritation when compared to the first topical pharmaceutical composition.

The disclosure also provides kits containing the pharmaceutical compositions described herein for use with the methods of treatment described herein.

A. Terms, Definitions and Abbreviations

As used herein and unless otherwise expressly noted or required by the context, all percentages refer to percentages by weight (wt-%) of the total composition (w/w).

As used herein in connection with a measured quantity, for example weight, "about" refers to that variation in the measured quantity as would be expected by one skilled in the art exercising a level of care commensurate with the objective of the measurement and the equipment used, and includes uncertainties that may be introduced by mathematical rounding errors.

As used herein an "anti-acne" compound is a compound that treats acne, for example, reducing the amount of acne. Anti-acne compounds include, but are not limited to, comedolytics (which help keratinization and thus prevent clogged pores), antibiotics (which generally target the acne-causing bacterium *Propionibacterium acnes* or *P. acnes*), and anti-inflammatory compounds (which have a direct effect on inflammation independent of any comedolytic or antibiotic effects). Non-limiting examples of comedolytics include alpha hydroxy acids (e.g., glycolic acid, lactic acid, and salicylic acid), retinoids (e.g., tretinoin and isotretinoin), and saturated dicarboxylic acids (e.g., suberic acid, azelaic acid, and sebacic acid). Non-limiting examples of antibiotics include cephalosporins (e.g., cefoxitin, ceftazidime, and cefepime), lincosamides (e.g., clindamycin and lincomycin), macrolides (e.g., erythromycin and azithromycin), pleuromutillins (e.g., retapamulin), metal complexes (e.g., zinc pyrithione, zinc methoxazole, and zinc sulfathiazole), penicillins (e.g., amoxicillin, ampicillin, and carbenicillin), fluoroquinolones (e.g., ciprofloxacin, clinafloxacin, ofloxacin, and trovafloxacin), retinoids (e.g., tretinoin), saturated dicarboxylic acids (e.g., suberic acid, azelaic acid, and sebacic acid), sulfonamides (e.g., sulfamethizole, sulfamethoxazole, sulfisoxazole), sulfones (e.g., dapsone or diaminodiphenyl sulfone), and tetracyclines (e.g., doxycycline and minocycline). Non-limiting examples of an anti-inflammatory compound include lincosamides (e.g., clindamycin and lincomycin), niacinamide (also known as nicotinamide and pyridine-3-corboxamide), retinoids (e.g., tretinoin), and saturated dicarboxylic acids (e.g., suberic acid, azelaic acid, and sebacic acid). For example, anti-acne compounds include azelaic acid, clindamycin, niacinamide, tretinoin, and zinc pyrithione, or a pharmaceutically acceptable salt thereof.

Saturated dicarboxylic acids can act as comedolytics and as antibiotics. Although azelaic acid is a preferred anti-acne compound for use in those embodiments of the present disclosure in which an anti-acne compound is included, other saturated dicarboxylic acids may also be used, including suberic acid and sebacic acid. Azelaic acid (also known as nonanedioic acid) is an external treatment for, for example, acne, rosacea, melasma, and postinflammatory hyperpigmentation. Azelaic acid is also used as an antifungal.

Lincosamides and macrolides are antibiotics that inhibit protein synthesis by binding to the 50S subunit of bacterial ribosomes and thus prevent bacteria from replicating. Although clindamycin is a preferred anti-acne compound for use in those embodiments of the present disclosure in which an anti-acne compound is included, other lincosamides can also be used, including lincomycin. Clindamycin is also known as (2S,4R)—N-[2-chloro-1-[(2R,3R,4S,5R,6R)-3,4, 5-trihydroxy-6-methylsulfanyloxan-2-yl]propyl]-1-methyl-4-propylpyrrolidine-2-carboxamide. In some embodiments, clindamycin is used with another antibiotic. An antibiotic combination may prevent antibiotic resistance in a subject.

Retinoids are well known to those skilled in the art of formulating topical dermatological compositions. Retinoids exhibit the pharmacological activity of all trans retinol and share, as a common structural feature, a β-ionone-type ring (2,6,6-trimethylcyclohen-1-ene) having a multiply unsaturated alkyl side chain at the 1 position of the ring. Tretinoin is the carboxylic acid form of vitamin A, so tretinoin (also known as all-trans retinoic acid) is a vitamin derivative. Although tretinoin is a preferred retinoid for use in those embodiments of the present disclosure in which a retinoid or an anti-acne compound is included, other retinoid derivatives can also be used, including adapalene, isotretinoin, or tazarotene.

Some metal complexes including zinc pyrithione have antibiotic effects. Although zinc pyrithione (also known as bis(2-pyridylthio)zinc 1,1'-dioxide) is a preferred anti-acne compound for use in those embodiments of the present disclosure in which an anti-acne compound is included, other metal complexes can also be used, including zinc methoxazole and zinc sulfathiazole. Zinc pyrithione is also used as an antifungal. Zinc pyrithione is used to treat and prevent UV-induced skin damage and may also treat hyperpigmentation such as melasma.

The term "anti-inflammatory" compound for the purposes of the present disclosure refers to a compound that reduces certain signs of inflammation and may treat inflammatory acne (e.g., papules, pustules, nodules, and cysts) independent of any comedolytic or antimicrobial effects. For example, anti-inflammatory compounds include azelaic acid, clindamycin, niacinamide, and tretinoin.

As used herein an "anti-photoaging" compound is a compound that treats photoaging, for example, reducing the amount of fine wrinkles or of hyperpigmentation. Anti-photoaging compounds include, but are not limited to, antioxidants (e.g., vitamins or vitamin derivatives including, but not limited to, niacinamide and ascorbyl phosphate, ascorbyl 6 palmitate, isostearyl 2-0 L-ascorbyl phosphate, and ascorbic acid sulfate) and tyrosinase inhibitors (e.g., 4-n-butylresorcinol, azelaic acid, and kojic acid). For example, anti-photoaging compounds include azelaic acid, niacinamide, and ascorbyl phosphate, or a pharmaceutically acceptable salt thereof (e.g., magnesium ascorbyl phosphate and sodium ascorbyl phosphate).

The term "antioxidant" for the purposes of the present disclosure refers to a chemical substance that is added to a pharmaceutical composition to treat or to prevent photoaging, for example, by inhibiting the oxidation of molecules that are present in skin or dermis of a subject. Vitamins and vitamin derivatives are well known to those skilled in the art of formulating topical dermatological compositions. Certain vitamin derivatives have increased stability over the naturally occurring form of the vitamin. For example, some vitamin E derivatives, including tocopheryl acetate, are more stable than the naturally occurring tocopherol (vitamin E), and some vitamin C derivatives, including ascorbyl phosphate, ascorbyl 6 palmitate, isostearyl 2-O L-ascorbyl phosphate, and ascorbic acid sulfate, or pharmaceutically acceptable salts thereof, are more stable than the naturally occurring L-ascorbic acid or ascorbate (vitamin C). Vitamin C is the most abundant antioxidant in the skin and is a cofactor in collagen production. Although magnesium ascorbyl phosphate is a preferred anti-photoaging compound for use in those embodiments of the present disclosure in which an anti-photoaging compound is included, other derivatives of vitamin C can also be used, including sodium ascorbyl phosphate and ascorbyl 6 palmitate. Niacinamide is a form of vitamin B3 that fights acne via anti-inflammatory properties and has anti-aging effects.

The term "tyrosinase inhibitor" for the purposes of the present disclosure refers to a chemical compound that is added to a pharmaceutical composition to treat or to prevent photoaging, for example, by reducing the production of melanin by binding to tyrosinase present in skin or dermis of a subject. Tyrosinase is a copper-containing oxidase that catalyzes the first two steps in the production of melanin. Overproduction of melanin can lead to hyperpigmentation. Although azelaic acid is a preferred anti-photoaging compound for use in those embodiments of the present disclosure in which an anti-photoaging compound is included, other tyrosinase inhibitor can also be used, including 4-n-butylresorcinol and kojic acid.

An "inactive ingredient" is compatible with the other ingredients of the formulation and not injurious to the patient or to the subject. Non-limiting examples of inactive ingredients include a preservative, a thickening agent, a vehicle, and a vitamin derivative.

The term "preservative" for the purposes of the present invention refers to a chemical substance that is added to a pharmaceutical composition to prevent the pharmaceutical composition from deterioration, decomposition or degradation or to substantially reduce or decelerate the degree and/or the speed of such deterioration, decomposition or degradation. Non-limiting examples of preservatives include benzoate, ethylhexylglycerin, methyl benzoate, methyl paraben, phenoxyethanol, propionic acid, propyl paraben, and pharmaceutically acceptable salts thereof.

The term "vehicle" refers to a substance that serves as a carrier, whether diluent or excipient, for improving the efficiency of delivery and the effectiveness of a pharmaceutical composition. The phrase "pharmaceutically acceptable vehicle" is art recognized and includes a pharmaceutically acceptable material, composition or vehicle, suitable for administering compounds of the present invention to mammals. The vehicles include liquid or solid filler, diluent, excipient, solvent or encapsulating material, involved in carrying or transporting the subject agent from one organ, or portion of the body, to another organ, or portion of the body. Each vehicle must be "acceptable" in the sense of being compatible with the other ingredients of the formulation and not injurious to the patient or to the subject. Some examples of materials which can serve as pharmaceutically acceptable vehicles include: water; aloe vera leaf juice; emulsifiers or thickening agents, such as carbomer, cetearyl alcohol, cetyl alcohol, glyceryl stearate, stearic acid, xanthan gum, and viscous liquids; sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter, myristyl myristate, Shea butter, and suppository waxes; oils, such as acai palm fruit oil, calendula flower oil, corn oil, cottonseed oil, jojoba seed oil, olive oil, passion fruit seed oil, peanut oil, rice bran oil, safflower oil, sesame oil, soybean oil, and sweet almond seed oil; glycols, such as propylene glycol; polyols, such as glycerin, vegetable glycerin, sorbitol, mannitol and polyethylene glycol (e.g., ceteareth-20 and PEG-100 myristate); esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As used herein, the term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

B. Embodiments

In one aspect, the current disclosure provides a composition comprising
a) a first anti-acne compound;
b) a second anti-acne compound; and
c) an anti-photoaging compound,
or a pharmaceutically acceptable salt thereof.

In certain embodiments, each of the first and second anti-acne compounds are selected from the group consisting of comedolytics and antibiotics. In some embodiments, the first and second anti-acne compounds are selected from the group consisting of cephalosporins, lincosamides, macrolides, pleuromutillins, metal complexes, penicillins, fluoroquinolones, niacinamide, retinoids, saturated dicarboxylic acids, sulfonamides, sulfones, and tetracyclines. In other embodiments, each of the first and second anti-acne compounds are selected from the group consisting of azelaic acid, clindamycin, niacinamide, tretinoin, and zinc pyrithione, or a pharmaceutically acceptable salt thereof. In some embodiments, one of the anti-acne compounds is an antibiotic. In other embodiments, each of the first and second anti-acne compounds are antibiotics. In further embodiments, one of the anti-acne compounds is an anti-inflammatory compound. In certain embodiments, the anti-inflammatory compound is selected from the group consisting of lincosamides, niacinamide, retinoids, and saturated dicarboxylic acids. In other embodiments, the anti-inflammatory compound is selected from the group consisting of azelaic acid, clindamycin, niacinamide, and tretinoin, or a pharmaceutically acceptable salt thereof.

In certain embodiments, the anti-photoaging compound is selected from the group consisting of an antioxidant and a tyrosinase inhibitor. In other embodiments, the anti-photoaging compound is selected from the group consisting of azelaic acid, niacinamide, and ascorbyl phosphate, or a pharmaceutically acceptable salt thereof.

In one embodiment, the composition comprises clindamycin, or a pharmaceutically acceptable salt thereof. In certain embodiments, the pharmaceutically acceptable salt of clindamycin is clindamycin phosphate. In other embodiments, the clindamycin, or a pharmaceutically acceptable salt thereof, can range, e.g., from about 0.1 to about 10%, and more usually 0.4 to 2% (e.g., 0.5 to 1.5%) of the composition w/w. For example, clindamycin phosphate may make up between 0.5 and 1.5% of the composition w/w.

In another embodiment, the composition comprises niacinamide, or a pharmaceutically acceptable salt thereof. In some embodiments, the niacinamide, or a pharmaceutically acceptable salt thereof, can range, e.g., from about 0.1 to about 15%, and more usually 2 to 8% (e.g., 2 to 6%) of the composition w/w.

In yet another embodiment, the composition comprises tretinoin, or a pharmaceutically acceptable salt thereof. In some embodiments, the tretinoin, or a pharmaceutically acceptable salt thereof, can range, e.g., from about 0.001 to about 1%, and more usually 0.005 to 0.3% (between, e.g., 0.005 and 0.2%, 0.009 and 0.15%, 0.017 and 0.1%, 0.01 to 0.1%, and 0.02 and 0.14%) of the composition w/w.

In other embodiments, the composition comprises zinc pyrithione, or a pharmaceutically acceptable salt thereof. In some embodiments, the zinc pyrithione, or a pharmaceutically acceptable salt thereof, can range, e.g., from about 0.01 to about 2%, and more usually 0.05 to 1% (e.g., 0.1 to 0.5%) of the composition w/w.

In still another embodiment, the composition comprises azelaic acid, or a pharmaceutically acceptable salt thereof. In some embodiments, the azelaic acid, or a pharmaceutically acceptable salt thereof, can range, e.g., from about 0.1 to about 25%, and more usually 3 to 20% (e.g., 4 to 20%) of the composition w/w.

In a further embodiment, the composition comprises a vitamin C derivative, or a pharmaceutically acceptable salt thereof. In certain embodiments, the pharmaceutically acceptable salt of a vitamin C derivative is magnesium ascorbyl phosphate. In some embodiments, the vitamin C derivative, or a pharmaceutically acceptable salt thereof, can range, e.g., from about 0.1 to about 25%, and more usually 1 to 15% (e.g., 3 to 10% and 2 to 8%) of the composition w/w.

In some embodiments, the first and second anti-acne compounds are different anti-acne compounds. In some embodiments the first and second anti-acne compounds are selected from the group consisting of azelaic acid and clindamycin; azelaic acid and niacinamide; azelaic acid and tretinoin; azelaic acid and zinc pyrithione; clindamycin and niacinamide; clindamycin and tretinoin; clindamycin and zinc pyrithione; niacinamide and tretinoin; niacinamide and zinc pyrithione; and tretinoin and zinc pyrithione, or pharmaceutically acceptable salts thereof.

In some embodiments, the first and second anti-acne compounds are different from the anti-photoaging compound. In other embodiments, a first anti-acne compound, a second anti-acne compound, and an anti-photoaging compound are three different compounds. In still other embodiments, if first or second anti-acne compound is azelaic acid, then the anti-photoaging compound is not azelaic acid. In further embodiments, if first or second anti-acne compound is niacinamide, then the anti-photoaging compound is not niacinamide. In another embodiment, if the anti-photoaging compound is azelaic acid, then neither the first nor the second anti-acne compounds are azelaic acid. In yet another embodiment, if the anti-photoaging compound is niacinamide, then neither the first nor the second anti-acne compounds are niacinamide.

In certain embodiments, the composition comprising a first anti-acne compound, a second anti-acne compound, and an anti-photoaging compound is selected from the group consisting of azelaic acid, clindamycin, and a vitamin C derivative; azelaic acid, clindamycin, and ascorbyl phosphate; azelaic acid, niacinamide, and a vitamin C derivative; azelaic acid, niacinamide, and ascorbyl phosphate; azelaic acid, tretinoin, and niacinamide; azelaic acid, tretinoin, and a vitamin C derivative; azelaic acid, tretinoin, and ascorbyl phosphate; azelaic acid, zinc pyrithione, and a vitamin C derivative; azelaic acid, zinc pyrithione, and ascorbyl phosphate; clindamycin, niacinamide, and azelaic acid; clindamycin, niacinamide, and a vitamin C derivative; clindamycin, niacinamide, and ascorbyl phosphate; clindamycin, tretinoin, and azelaic acid; clindamycin, tretinoin, and niacinamide; clindamycin, tretinoin, and a vitamin C derivative; clindamycin, tretinoin, and ascorbyl phosphate; clindamycin, zinc pyrithione, and azelaic acid; clindamycin, zinc pyrithione, and niacinamide; clindamycin, zinc pyrithione, and a vitamin C derivative; clindamycin, zinc pyrithione, and ascorbyl phosphate; niacinamide, tretinoin, and azelaic acid; niacinamide, tretinoin, and a vitamin C derivative; niacinamide, tretinoin, and ascorbyl phosphate; niacinamide, zinc pyrithione, and azelaic acid; niacinamide, zinc pyrithione, and a vitamin C derivative; niacinamide, zinc pyrithione, and ascorbyl phosphate; tretinoin, zinc pyrithione, and azelaic acid; tretinoin, zinc pyrithione, and niacinamide; tretinoin, zinc pyrithione, and a vitamin C derivative; and tretinoin, zinc pyrithione, and ascorbyl phosphate, or pharmaceutically acceptable salts thereof. In some embodiments, the composition comprises tretinoin, ascorbyl phosphate, and azelaic acid.

In certain embodiments, the anti-photoaging compound is selected from the group consisting of an antioxidant and a tyrosinase inhibitor. In some embodiments, the anti-photoaging compound is not a steroid or a bleaching agent (e.g., hydroquinone). In other embodiments, the anti-photoaging compound is selected from the group consisting of azelaic acid, niacinamide, and ascorbyl phosphate, or a pharmaceutically acceptable salt thereof.

In some embodiments the composition comprises a first and a second anti-acne compounds selected from the group consisting of 0.5 to 1.5% clindamycin, 2 to 6% niacinamide, 0.005 to 0.3% tretinoin, and 0.1 to 0.5% zinc pyrithione, or a pharmaceutically acceptable salt thereof; and an anti-photoaging compound selected from the group consisting of 4 to 20% azelaic acid; 2 to 6% niacinamide, and 3 to 10% a vitamin C derivative, or a pharmaceutically acceptable salt thereof. In some embodiments, the composition comprises 2 to 6% niacinamide, 0.005 to 0.3% tretinoin, and 3 to 10% of a vitamin C derivative of the composition w/w. For example, the composition may comprise about 4% niacinamide, 0.005 to 0.3% tretinoin, and about 5% of a vitamin C derivative; about 4% niacinamide, 0.005 to 0.3% tretinoin, and about 5% magnesium ascorbyl phosphate, of the composition w/w.

In certain embodiments, the composition further comprises a pharmaceutically acceptable vehicle. In some embodiments, the composition further comprises one or more inactive ingredients. In other embodiments, at least one inactive ingredient is a pharmaceutically acceptable vehicle. In still other embodiments, at least one inactive ingredient is a preservative. In some embodiments, the composition further comprises at least one pharmaceutically acceptable vehicle, at least one emulsifier, at least one excipient, at least one oil, at least one polyol, and at least one preservative. In certain embodiments, the composition further comprises one or more of the following inactive ingredients water, vegetable glycerin, stearic acid, myristyl myristate, cetearyl alcohol, ceteareth-20, glyceryl stearate, jojoba seed oil, soybean oil, cetyl alcohol, carbomer, shea butter, calendula flower oil, passion fruit seed oil, rice bran oil, acai palm fruit oil, phenoxyethanol, ethylhexylglycerin. In one embodiment, the composition further comprises the following inactive ingredients water, glycerin, aloe vera leaf juice, PEG-100 myristate, sweet almond seed oil, xanthan gum, methyl paraben, propyl paraben, and tocopheryl acetate.

In certain embodiments, a first anti-acne compound, a second anti-acne compound, and an anti-photoaging compound are administered simultaneously. In some embodiments, a first anti-acne compound, a second anti-acne compound, and an anti-photoaging compound are active at the same pH or in the same pH range. In other embodiments, the pH of the composition can range, e.g., from about 3.0 to about 7.0, and more usually from about 3.5 to about 6.0 (e.g., from 4.0 to 5.0).

In some embodiments, the composition batch size can range, e.g., from about 5 g to about 100 kg, and more usually 100 g to 10 kg (e.g., 0.5 kg to 3 kg). In certain embodiments, the composition batch is divided into 30 g aliquots. In some embodiments, the composition batch size can range, e.g., from about 5 mL to about 100 L, and more usually 100 mL to 10 L (e.g., 0.5 L to 3 L). In certain embodiments, the composition batch is divided into 30 mL aliquots.

In another aspect, the current disclosure provides a composition comprising a first antibiotic, a second antibiotic and a vitamin or a vitamin derivative, or a pharmaceutically acceptable salt thereof.

In certain embodiments, the first and second antibiotics are distinct antibiotics. In some embodiments, each of the first and second antibiotics are selected from the group consisting of lincosamides, metal complexes, and saturated dicarboxylic acids. In certain embodiments, each of the first and second antibiotics are selected from the group consisting of azelaic acid, clindamycin, and zinc pyrithione. In still other embodiments, the vitamin or a vitamin derivative, or a pharmaceutically acceptable salt thereof, are selected from the group consisting of tretinoin, niacinamide, a vitamin C derivative (e.g., ascorbyl phosphate).

In certain embodiments, the composition comprising a first antibiotic, a second antibiotic and a vitamin or a vitamin derivative, or a pharmaceutically acceptable salt thereof, is selected from the group consisting of azelaic acid, clindamycin, and tretinoin; azelaic acid, clindamycin, and niacinamide; azelaic acid, clindamycin, and a vitamin C derivative; azelaic acid, zinc pyrithione, and tretinoin; azelaic acid, zinc pyrithione, and niacinamide; azelaic acid, zinc pyrithione, and a vitamin C derivative; clindamycin, zinc pyrithione, and tretinoin; clindamycin, zinc pyrithione, and niacinamide; and clindamycin, zinc pyrithione, and a vitamin C derivative, or pharmaceutically acceptable salts thereof.

In a further aspect, the current disclosure provides a composition comprising a first anti-inflammatory, a second anti-inflammatory, and an antifungal or an antioxidant, or a pharmaceutically acceptable salt thereof.

In some embodiments, each of the first and second anti-inflammatory compounds are selected from the group consisting of lincosamides, niacinamide, retinoids, and saturated dicarboxylic acids. In other embodiments, each of the first and second anti-inflammatory compounds are selected from the group consisting of azelaic acid, clindamycin, niacinamide, and tretinoin, or a pharmaceutically acceptable salt thereof.

In other embodiments, the antifungal is selected from the group consisting of azelaic acid, ketoconazole, and zinc pyrithione, or a pharmaceutically acceptable salt thereof. In still other embodiments, the antioxidant is selected from the group consisting of niacinamide and a vitamin or a vitamin derivative, or a pharmaceutically acceptable salt thereof. In certain embodiments, the antioxidant is selected from the group consisting of niacinamide and a vitamin C derivative (e.g., ascorbyl phosphate).

In other embodiments, the composition is administered topically. The topical compositions of the present disclosure can be provided in the form of a cream (ointment), a gel, or lotion. Creams are particularly preferred. The pharmaceutically acceptable vehicle is selected according to the desired final form of the topical composition (cream or ointment, gel, lotion, and the like) from the types of vehicles known in the art for topical application of active ingredients.

In some embodiments, the frequency of application of the disclosed compositions to the skin of a subject may be one, two, or three times per day. In certain embodiments, the frequency of application is once per day.

In another aspect, the current disclosure provides a method for the treatment of acne and photoaging in a subject in need thereof comprising administering to the skin of the subject a composition comprising
  a) a first anti-acne compound;
  b) a second anti-acne compound, wherein each of the first and second anti-acne compounds are selected from the group consisting of azelaic acid, clindamycin, niacinamide, tretinoin, and zinc pyrithione, or a pharmaceutically acceptable salt thereof;
  c) an anti-photoaging compound, wherein the anti-photoaging compound is selected from the group consisting of azelaic acid, niacinamide, and ascorbyl phosphate, or a pharmaceutically acceptable salt thereof; and
  d) a pharmaceutically acceptable vehicle,
  wherein the first anti-acne compound, the second anti-acne compound, and the anti-photoaging compound are three different compounds.

In yet another aspect, the current disclosure provides a method for the treatment of acne and photoaging in a subject in need thereof comprising
  a) administering to the skin of the subject a first composition, wherein the first composition comprises less than 0.025% tretinoin and less than 12% azelaic acid;
  b) evaluating the skin of the subject after a first interval; and
  c) administering a second composition comprising a higher concentration of tretinoin or azelaic acid or both than the first composition if the acne or photoaging requires further improvement,
  thereby treating acne and photoaging in the subject.

In some embodiments, a first composition is administered to the skin of a subject. In some embodiments, the first composition is selected from the group consisting of clindamycin, niacinamide, and azelaic acid; clindamycin, niacinamide, and a vitamin C derivative; clindamycin, niacinamide, and ascorbyl phosphate; clindamycin, tretinoin, and azelaic acid; clindamycin, tretinoin, and niacinamide; clindamycin, tretinoin, and a vitamin C derivative; clindamycin, tretinoin, and ascorbyl phosphate; clindamycin, zinc pyrithione, and azelaic acid; clindamycin, zinc pyrithione, and niacinamide; clindamycin, zinc pyrithione, and a vitamin C derivative; clindamycin, zinc pyrithione, and ascorbyl phosphate; niacinamide, tretinoin, and azelaic acid; niacinamide, tretinoin, and a vitamin C derivative; niacinamide, tretinoin, and ascorbyl phosphate; niacinamide, zinc pyrithione, and azelaic acid; niacinamide, zinc pyrithione, and a vitamin C derivative; niacinamide, zinc pyrithione, and ascorbyl phosphate; tretinoin, zinc pyrithione, and azelaic acid; tretinoin, zinc pyrithione, and niacinamide; tretinoin, zinc pyrithione, and a vitamin C derivative; and tretinoin, zinc pyrithione, and ascorbyl phosphate, or pharmaceutically acceptable salts thereof.

In other embodiments, the first composition is a less irritating formulation, for example, the first composition comprises little or no tretinoin and azelaic acid. In further embodiments, the first composition does not include tretinoin or azelaic acid. In certain embodiments, the first composition comprises less than 0.025% tretinoin and less than 12% azelaic acid. In some embodiments, the first composition comprises clindamycin, zinc pyrithione, and niacinamide. In certain embodiments, the first composition comprises clindamycin, azelaic acid, and niacinamide.

In some embodiments, evaluating the skin of the subject includes evaluating skin brightness, discoloration, fine lines, and wrinkles. In certain embodiments, evaluating the skin of the subject includes one or more of the following: creation and use of a portal (e.g., through the internet), which allows secure examination of high-resolution photographs; remote examination of high-resolution photographs; and in person examination by a qualified grader. In other embodiments, evaluating the skin of the subject is a form of telemedicine via secure uploading of the subject's medical history and digital high-resolution photographs online or through the internet. In still other embodiments, evaluating the skin of the subject includes evaluating skin by profilometry; evaluating skin tone; evaluating skin color; evaluating skin firmness; evaluating skin elasticity; evaluating skin hydration; and evaluating skin aging by visual assessments. In some embodiments, evaluating the skin of the subject includes one or more of the following: profilometric analysis; measurements with a CUTOMETER® MPA 580; measurements with a CHROMAMETER CR300®; measurements with a CORNEOMETER® CM825; expert visual assessments; and visual assessments with Visia CR Capture.

In some embodiments, effects including, but non-limited to, anti-wrinkle, visible reduction of fine lines and wrinkles, reduction of the appearance of fine lines and wrinkles, skin firming, improvement in skin texture, improvement in the skin's elasticity, improvement in skin luminosity, reduction of uneven pigmentation, hydrating, moisturizing, combating skin dehydration, and encouraging even skin tone are evaluated after an interval of time. In other embodiments, improvement of acne, e.g., less acne, or of photoaging, e.g., less discoloration, fine lines, and/or wrinkles, is evaluated after an interval of time. The interval of time can range, e.g., from about 1 day to about a year, and more usually 1 week to 6 months (e.g., 4, 8, and 12 weeks). In some embodiments, the first interval is four weeks. In other embodiments, evaluating the skin of the subject occurs at one or more intervals of time over the course of treatment. In some embodiments, the method of treatment of acne and photoaging in a subject in need thereof is applied over a period of time that can range, e.g., from about 1 day to about 50 years, and more usually 1 week to about 25 years (e.g., 3 months, 6 months, 1 year, 5 years, and 10 years).

In other embodiments, the acne is caused by P. acnes. In other embodiments, the antimicrobial may target one or more of the following bacteria P. acnes, Staphylococcus aureus, and Staphylococcus epidermis.

In some embodiments, the acne is non-inflammatory acne, also known as comedones, (e.g., blackheads and white heads). In other embodiments, the acne is inflammatory acne (e.g., papules, pustules, nodules, and cysts). In still other embodiments, the acne is a combination of non-inflammatory acne and inflammatory acne.

In certain embodiments, the acne may be classified by its severity. When a subject has several comedones but very few papules and pustules, then the subject has mild acne. If a subject has a mix of comedones and several inflamed papules and pustules existing together, the acne is mild to moderate acne. If a subject has also has some nodules along with papules and pustules, the acne is moderate acne. Deep cysts or any type of acne that leaves behind permanent pitted or saucer-shaped scars is categorized as severe acne. In certain embodiments, evaluating the skin of the subject includes evaluating the severity of the acne.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved In some embodiments, a second composition is administered to the skin of a subject upon evaluation of the skin of the subject after a first interval of time. In certain embodiments, the acne or photoaging has not improved, so a second composition comprising a higher concentration of tretinoin or azelaic acid compared to the first composition is administered to the skin of a subject. In some embodiments, the second composition comprises a higher concentration of tretinoin than previously administered to the subject in the first composition. For example, the concentration of tretinoin may increase from 0% to 0.009, 0.012, 0.017, 0.018, 0.02, 0.035, 0.04, 0.05, 0.06, 0.07, 0.09, 0.1, 0.14, or 0.15% of the composition w/w. In certain embodiments, the second composition comprises clindamycin, niacinamide, and azelaic acid. In other embodiments, the second composition comprises clindamycin, tretinoin, and azelaic acid. In further embodiments, the second composition comprises tretinoin, zinc pyrithione, and azelaic acid. In another embodiment, the second composition comprises tretinoin, azelaic acid, and a vitamin C derivative.

In other embodiments, a third composition is administered to the skin of a subject upon evaluation of the skin of the subject after a second interval of time. In certain embodiments, the acne or photoaging has not improved, so a third composition that fine tunes the treatment of acne or improves the treatment of photoaging is administered to the skin of a subject. In other embodiments, the third composition comprises clindamycin, tretinoin, and azelaic acid. In further embodiments, the third composition comprises tretinoin, zinc pyrithione, and azelaic acid. In another embodiment, the third composition comprises tretinoin, azelaic acid, and a vitamin C derivative.

In certain embodiments, more than two compositions are administered to the skin of the subject in a method for the treatment of acne and photoaging in a subject in need thereof. The skin of the subject is evaluated after an interval of time, and a different composition is administered to the subject. Each composition administered to the subject after the first composition or after the second composition comprises tretinoin. In some embodiments, the composition comprises a higher concentration of tretinoin than previously administered to the subject. For example, the concentration of tretinoin may increase from 0% to 0.009, 0.012, 0.017, 0.018, 0.02, 0.035, 0.04, 0.05, 0.06, 0.07, 0.09, 0.1, 0.14, or 0.15% of the composition w/w. However, the increase in the concentration of tretinoin may not be strictly sequential, that is, any composition comprising a higher concentration of tretinoin than the concentration of tretinoin previously administered to the subject may be used (e.g., 0.09% to 0.018%; 0.012% to 0.035%; 0.017% to 0.35%; 0.04% to 0.1%; 0.05% to 0.1%; and 0.06% to 0.14% of the composition w/w).

It will be understood by those having ordinary skill in the art that the specific dose level and frequency of dosage for any particular patient or subject may be varied and will depend upon a variety of factors including the activity of the specific composition employed, the metabolic stability and length of action of that composition, the age, body weight, general health, gender, diet, and the severity of the particular dermatological condition being treated. In addition specific dose level and frequency of dosage for any particular patient also may depend on factors including, but not limited to, skin sensitivity, other medications, acne type, allergies, and prior experiences with dermatologic treatments. For example, some patients may be treated using methods of this disclosure over a period of years if the acne or photoaging is a chronic condition.

In additional embodiments, pharmaceutical kits are provided. The kit includes a sealed container approved for the storage of pharmaceutical compositions, the container containing one of the above-described pharmaceutical compositions. In some embodiments, the sealed container minimizes the contact of air with the ingredients, e.g. an airless bottle. In other embodiments, the sealed container is a sealed tube. In certain embodiments, the sealed container is not a pump bottle. An instruction for the use of the composition and the information about the composition are to be included in the kit.

The following examples are provided to further elucidate the advantages and features of the present application, but are not intended to limit the scope of the application. The examples are for the illustrative purposes only. USP pharmaceutical grade products were used in preparing the formulations described below.

Example 1. Preparing a Pharmaceutical Composition

Pharmaceutical compositions were prepared as described below. The following products were used in the amounts and concentrations specified, sufficient to prepare 500 g. A composition comprising a first anti-acne compound, a second anti-acne compound, and an anti-photoaging compound was prepared according to the following formulation:

TABLE 1

Exemplary Composition A

| Ingredient | % of the Composition w/w |
| --- | --- |
| Tretinoin | 0.02 |
| Niacinamide | 4 |
| Magnesium ascorbyl phosphate | 5 |
| Water | |
| Glycerin | |
| Aloe vera leaf juice | |
| PEG-100 myristate | |
| Sweet almond seed oil | |
| Methyl paraben | |
| Propyl paraben | |
| Tocopheryl acetate | |

Compositions comprising a first anti-acne compound, a second anti-acne compound, and an anti-photoaging compound were prepared according to the following formulations:

In Tables 2 (see FIG. 1) and 3, the abbreviations used are as follows: azelaic acid (AzA); clindamycin (Clinda); niacinamide (Nia); tretinoin (Tret); magnesium ascorbyl phosphate (VitC); and zinc pyrithione (Zinc). In Table 2 (see FIG. 1), the percentage values correspond to the amount of tretinoin by % of the composition w/w. The shading of the Table 2 in FIG. 1 corresponds to the potential of the composition to cause irritation to the skin of the subject with darker grays corresponds to higher potential to cause irritation.

Compositions comprising a first anti-acne compound, a second anti-acne compound, and an anti-photoaging compound were prepared according to the following formulations:

TABLE 3

Exemplary pharmaceutical compositions, Compositions R-W.

| Formulation | Formulation Active Ingredients |
| --- | --- |
| Composition R | 1% Clinda, 4% AzA, 0.25% Zinc |
| Composition S | 1% Clinda, 4% Nia, 0.25% Zinc |
| Composition T | 1% Clinda, 4% Nia, 4% AzA |
| Composition U | 1% Clinda, 4% Nia, 0.25% Zinc |
| Composition V | 1% Clinda, 4% Nia, 4% AzA |
| Composition W | 0.02% Tretinoin, 4% Niacinamide |

The compositions also may comprise the components listed in Table 2 or in Table 3 above and further comprise at least one pharmaceutically acceptable vehicle, at least one emulsifier, at least one excipient, at least one oil, at least one polyol, and at least one preservative.

Example 2. Stability Data for Pharmaceutical Compositions

The compositions prepared according to the formulations as described in Example 1, Table 3 were then analyzed for the stability of the compositions over time.

TABLE 4

Percent change in total active ingredients measured and calculated for various example compositions of the invention.

| | Active Ingredient Stability Ratio at Room Temp. | | |
| --- | --- | --- | --- |
| Formulation Description | T0 | 1 month | 3 months |
| 1% Clindamycin | 0.00 | 0.952 | 0.868 |
| 1% Clinda, 2% Ketoconazole | 0.00 | 0.981 | 0.952 |
| 1% Clinda, 4% AzA, 0.25% Zinc | 0.00 | | 1.028 |
| 1% Clinda, 4% Nia, 0.25% Zinc | 0.00 | | 0.931 |
| 1% Clinda, 4% Nia, 0.25% AzA | 0.00 | | 0.902 |
| 4% Niacinamide | 0.00 | 0.9908 | |
| 0.02% Tretinoin, 4% Niacinamide | 0.00 | 0.991 | |
| 1% Clinda, 4% Nia, 0.25% Zinc | 0.00 | | 1.078 |
| 1% Clinda, 4% Nia, 0.25% AzA | 0.00 | | 1.045 |
| 0.02% Tretinoin | 0.00 | 1.048 | |
| 0.02% Tretinoin, 4% Niacinamide | 0.00 | 0.903 | |
| 0.06% Tretinoin, 4% Nia, 5% VitC | 0.00 | 0.981 | 0.948 |

In the above table, the abbreviations used are as follows: azelaic acid (AzA); clindamycin (Clinda); niacinamide (Nia); magnesium ascorbyl phosphate (VitC); and zinc pyrithione (Zinc). Table 4 shows the percent change in total active ingredients measured and calculated for example compositions of the invention. To obtain the data in Table 4, each composition was maintained at room temperature for various time periods (about 1 and about 3 months) before measuring the stability of the active ingredients according to the following method.

The stability of the active ingredients was calculated based on HPLC data using the following equation:

$$\frac{(\text{Measured \% of Active ingredient after a time period})}{(\text{Initial Measured \% of Active ingredient})}$$

The compositions remained stable over a time interval of about 100 days. The active ingredients were not degraded or deactivated.

Example 3. Evaluating the Skin by Profilometry

The skin of the subject was evaluated based on profilometry. Subjects were positioned on their backs with their head in line with the midline of their body. They were asked to close their eyes and maintain a neutral expression. Test sites on the skin of the subject were located using replica locating rings ensuring that each ring lay flat on the skin. The skin was not stretched or pulled during ring placement. Each ring was placed on the left and right periorbital areas of the face with the tab directed towards the back of the head. The foam and paper portions of each ring were aligned. Subjects were asked to turn their head so that the side of the head being evaluated was as horizontal as possible. The transparency film was then placed over the subject's face. Full locating rings, with centers, were then placed onto the film exactly over the site which had been selected. Landmarks were then traced onto the film using an indelible marker pen. The film was then removed from the face and labelled to identify the subject. The film was stored in a cool, dry location until next use.

Replica Generation

The subject was placed in an identical manner to that described above and landmarks on the transparency film were lined up with the subject's facial features. A skin marker pen was then used to make dots through the film onto the face of the subject to enable exact location of the test sites. The ring was then positioned on the face, and the replicas generated by filling the well in the center of the ring with SILFLO® (JS Davis, Hert) material. Once the replica had set completely (approximately 5 minutes), it was removed from the skin, allowed to dry skin side up for a few minutes, and then placed in a storage sleeve.

Profilometric Analysis

The following equipment and software was used: PC: IBM compatible Pentium III 500 MHz with 256 MB memory running under Windows 2000 Professional. Video: Cohu solid state B&W camera, 50 mm lens/30 mm extension, Coreco TCI; Ultra frame grabber. OPTIMAS v6.5, Microsoft EXCEL 2000, StatSoft STATISTICA 6. A collimated light source directed at a 25° angle from the plane of the replica was used.

The replica was placed in a holder that fixed the direction of the tab position of the replica so that the replica could be rotated to align the tab direction normal or parallel to the incident light direction. The replicas were taken from the crow's feet area adjacent to each eye with the tab direction pointing toward the ear. The NORMAL sampling orientation provides texture measurements sensitive to the MAJOR, expression-induced lines (crow's feet). The PARALLEL sampling orientation provides texture measurements sensitive to the MINOR, fine lines. The general background gradient of light intensity was adjusted by applying a 1st order correction in the direction of the light propagation. The shadow texture produced by the oblique lighting of the negative replica was analysed by two types of assay methods:

Method A

Measuring the luminance along a set of 10 equal length parallel lines (passes) running across the replica parallel to the lighting direction. The variations in luminance were treated as indicative of the roughness and analyzed by traditional surface roughness statistics:

Rz—the average maximum difference in luminance value for five equal length segments in each of the 10 lines traversing the sample.

Ra—the average deviation of the luminance curve about the mean luminance for the same 10 lines.

The "R" parameters are reported in the units of brightness (Grey Levels) ranging from 0 to 255.

FSpace—distance between markers placed on the lines at luminance changes indicative of fine lines.

FNum—number markers per mm placed on the lines at luminance changes indicative of fine lines.

Method B

The replica image area was then divided into 10 equal width bands or sub-areas. The shadow-like features were detected in each of these bands according to their luminance values being less than the detection threshold. Four parameters were determined from the detected features.

Spacing—the mean distance in millimeters between adjacent detected features (i.e., spacing between the midpoints of adjacent shadowy features).

Breadth—the average breadth in millimeters of the detected features in millimeters. This parameter is proportional to the depth of the wrinkle producing the shadow.

Shadows—percent of the sampled replica area with luminance values less than the detection threshold. This is the relative area of shadows cast by the wrinkles and fine lines in the replica.

NumWr—the total number of features detected in the 10 bands or sub-areas used to calculate spacing and breadth.

Example 4. Evaluating the Skin Firmness and Elasticity

The skin of the subject was evaluated based on measurements to study any changes in the viscoelastic properties of the skin by the compositions of the disclosure were performed using the CUTOMETER® MPA 580 (Courage and Khazaka, Germany). The measuring principle is based on the suction method. Negative pressure is created in the device, and the skin is drawn into the aperture of the probe. Inside the probe, the penetration depth is determined by a noncontact optical measuring system. This optical measuring system consists of a light source and a light receptor, as well as two prisms facing each other, which project the light from transmitter to receptor. The light intensity varies due to the penetration depth of the skin. The resistance of the skin to be sucked up by the negative pressure (firmness) and its ability to return into its original position (elasticity) are displayed as curves at the end of each measurement using MICROSOFT WINDOWS® based software.

Example 5. Evaluating the Skin Tone and Color

The skin of the subject was evaluated based on instrumental measurements of skin tone and color were performed using a CHROMAMETER CR300® (Courage and Khazaka, Germany) in person. The measuring head of the CR-300 uses diffuse illumination/0° viewing geometry. A pulsed xenon arc (PXA) lamp inside a mixing chamber provides diffuse, uniform lighting over the 8 mm-diameter specimen area. Only the light reflected perpendicular to the specimen surface is collected by the optical-fiber cable for color analysis. This instrument measures the amount of light reflected from the skin and quantifies this into a numerical value using the $L^*a^*b^*$ color scale, where $L^*(100)$ equates to total white and $L^*(0)$ equates to total black. Therefore, the $L^*$ value is inversely proportional to the Fitzpatrick visual scale of skin tone. The instrument was allowed to warm up for 30 minutes prior to use.

Example 6. Evaluating the Skin Hydration

The skin of the subject was evaluated based on moisturization measurements to study the humectant properties of the compositions of the disclosure were performed using the CORNEOMETER® CM825 (Courage and Khazaka, Germany). This instrument relies on the dielectric constant, a physical property of water, which is relatively high and as such will affect the capacitance of a capacitor. Any change in the dielectric constant due to skin moisture variations will alter the capacitance of the precision capacitor in the instrument. These variations are detected electronically and are converted into a value by the CORNEOMETER®. A 15 minute warm-up period was allowed before using the CORNEOMETER®.

Three measurements were made using the probe attachment of the CORNEOMETER® at each of the test sites on the skin of the subject, between each assessment the probe attachment of the Corneometer® was pressed onto a dry tissue. The next assessment was not performed until a value of 5 or less was displayed by the instrument. Subjects must have been in the controlled environment (at a temperature of 22° C.±2° C. and at a relative humidity of 45%±5%) for at least 30 minutes prior to any assessments being performed.

Example 7. Evaluating the Skin by Expert Visual Assessment

The skin of the subject was evaluated by the same qualified grader at each time-point for the duration of the study according to the Glogau Classification of Aging scale (see Table 5). Illumination of the test sites on the skin of the subject was by a 60 watt pearl bulb placed approximately 30 cm from the test site on the skin of the subject.

TABLE 5

The Glogau Classification of Aging scale

| Group | Classification | Typical Age | Description | Skin Characteristics |
|---|---|---|---|---|
| I | Mild | 28-35 | No wrinkles | Early Photoaging: mild pigment changes, no keratosis, minimal wrinkles, minimal or no makeup |
| II | Moderate | 35-50 | Wrinkles in motion | Early to Moderate Photoaging: Early brown spots visible, keratosis palpable but not visible, parallel smile lines begin to appear, wears some foundation |
| III | Advanced | 50-65 | Wrinkles at rest | Advanced Photoaging: Obvious discolorations, visible capillaries (telangiectasias), visible keratosis, wears heavier foundation always |
| IV | Severe | 60-75 | Only wrinkles | Severe Photoaging: Yellow-gray skin color, prior skin malignancies, wrinkles throughout - no normal skin, cannot wear makeup because it cakes and cracks |

Example 8. Evaluating the Skin by Visual Assessment with Visia CR Capture

The skin of the subject was photographed and could be evaluated by the same qualified grader at each time-point for the duration of the study according to the Glogau Classification of Aging scale (see Table 5). The Visia-CR captures multiple lighting modalities in one computer-controlled sequence. Subjects can be photographed using standard light, UV, cross-polarization and parallel polarization techniques. The Visia-CR was used to capture one full-face, and two side-view images (one left side and one right side), high-resolution digital image of each subject with their eyes closed. Subjects were instructed to remain in a relaxed state while photos were captured using the Visia-CR equipment.

Example 9. Clinical Study with a Composition

The composition prepared as described in Example 1, Table 1 was then evaluated for effects for treatment of acne and photoaging. A test composition comprised 0.02% tretinoin, 4% niacinamide, and 5% magnesium ascorbyl phosphate of the composition w/w. The test composition was evaluated in a single-blind, bi-lateral facial site, study in subjects aged at least 35 years with aged skin compared to an untreated site. There were 29 subjects recruited into the study, and 23 healthy subjects, who completed the study. Usage was evaluated over a time interval of 12 weeks. Aged skin included moderate hyperpigmentation or photoaging in the face, hands, or décolletage areas (minimum of Grade II on Glogau classification scale, see Table 5).

Exclusion criteria included one or more of the following pregnancy or lactation; inadequate or non-existent contraception (women of child bearing potential only); a current skin disease of any type apart from mild facial acne (e.g. eczema, psoriasis); heavy alcohol consumption (i.e. more than 14 units per week or 4 units a day); current use or history of repeated use of street drugs; a febrile illness lasting more than 24 hours in the six days prior to study commencement; significant past medical history of hepatic, renal, cardiac, pulmonary, digestive, haematological, neurological, locomotor or psychiatric disease; history of asthma only if requiring regular medication or hay fever that required prescription treatment in two or more of the previous three years; a history of multiple drug hypersensitivity; concurrent medication likely to affect the response to the test articles or confuse the results of the study; known sensitivity to the test articles or their constituents including packaging materials; current treatment by a physician for allergy unless physician consulted and participation approved; participation in a skin lightening or anti-ageing study in the month prior to study state date; recent immunization (less than 10 days prior to test commencement); a medical history indicating atopy (tendency to develop allergic diseases including eczema); no microdermabrasion treatment or superficial/light chemical peel on any study site within 30 days prior to the study period; and no use of prescription skin creams containing tretinoin or use of non-prescription retinol containing skin creams.

Prohibitions and restrictions for the duration of the study included no use of sun beds or sun lamps for the duration of the study; no immunization from ten days prior to first assessment and product usage until completion of the study; no use of anti-ageing products/treatments for the duration of the study in the assessed areas other than those issued/allocated; and discontinue use of any products containing hydroquinone, glycolic acid, alpha-hydroxy acids, salicylic acid, retinol, peptides and ascorbic acid (vitamin C including derivatives) for the study duration.

TABLE 6

Some demographic information on the subjects

| Age Range | No. of Females | No. of Males |
|---|---|---|
| 36-40 | 5 | 0 |
| 41-45 | 5 | 0 |
| 46-50 | 3 | 0 |
| 51-55 | 4 | 0 |
| 56-60 | 0 | 2 |
| 61+ | 7 | 1 |

Profilometery assessments were performed according to the methods described in Example 3. Profilometery assessments of the visible appearance of fine lines and wrinkles show a highly statistically significant improvement at all time-points of the study with a reduction in the appearance of fine lines and wrinkles of 4.35% (week 4), 6.47% (week 8) and 8.55% (week 12) (Table 7). The untreated control site showed no statistically significant reduction in the appearance of fine lines and wrinkles at any timepoint of the study compared to baseline measurements (Table 8).

TABLE 7

Profilometery data for treated areas of the skin of the subjects

| | Treated | | | |
|---|---|---|---|---|
| | Baseline | Week 4 | Week 8 | Week 12 |
| Mean | 94.04 | 89.96 | 87.95 | 86.00 |
| % Difference to baseline | | −4.35% | −6.47% | −8.55% |
| % Difference to previous | | −4.35% | −2.23% | −2.22% |
| p-Value against Baseline | | 9.17E−14 | 1.93E−11 | 9.91E−12 |

TABLE 8

Profilometery data for untreated areas of the skin of the subjects

| | Untreated | | | |
|---|---|---|---|---|
| | Baseline | Week 4 | Week 8 | Week 12 |
| Mean | 93.09 | 93.00 | 93.14 | 92.61 |
| % Difference to baseline | | −0.09% | 0.05% | −0.51% |
| % Difference to previous | | −0.09% | 0.15% | −0.57% |
| p-Value against Baseline | | 8.06E−01 | 7.54E−01 | 1.26E−01 |

CUTOMETER® assessments were performed according to the methods described in Example 4. CUTOMETER® assessments of skin firmness and elasticity show a highly statistically significant improvement in both skin firmness and skin elasticity as shown in the below table for the treated site (Table 9). Following 12 weeks of use an improvement of 60.34% was observed at the treated site. The untreated control site showed no significant change in skin firmness or elasticity at any time-point during the trial validating the data (Table 10).

TABLE 9

CUTOMETER ® data for treated areas of the skin of the subjects

| | Treated | | | |
|---|---|---|---|---|
| | Baseline | Week 4 | Week 8 | Week 12 |
| Mean | 0.53 | 0.64 | 0.73 | 0.85 |
| % Difference to baseline | | 20.71% | 37.74% | 60.34% |
| % Difference to previous | | 20.71% | 14.11% | 16.41% |
| p-Value against Baseline | | 2.42E−11 | 9.25E−16 | 2.07E−19 |

TABLE 10

CUTOMETER ® data for untreated areas of the skin of the subjects

| | Untreated | | | |
|---|---|---|---|---|
| | Baseline | Week 4 | Week 8 | Week 12 |
| Mean | 0.53 | 0.53 | 0.53 | 0.53 |
| % Difference to baseline | | 0.16% | −0.02% | 0.31% |
| % Difference to previous | | 0.16% | −0.19% | 0.33% |
| p-Value against Baseline | | 3.96E−05 | 1.15E−06 | 7.97E−05 |

CHROMAMETER CR300® assessments were performed according to the methods described in Example 5. CHROMAMETER CR300® assessments of skin tone and coloration showed no significant lightening of the area around the treated area at any time-points. No positive statistically improvement was observed at any time point as shown in the summary tables below (Tables 11 and 12). At week 12 the untreated site showed a minimally statistical darkening of the test site compared to baseline values.

TABLE 11

CHROMAMETER CR300 ® data for treated areas of the skin of the subjects

| | Treated | | | |
|---|---|---|---|---|
| | Baseline | Week 4 | Week 8 | Week 12 |
| Mean | 60.48 | 90.97 | 60.06 | 59.14 |
| % Difference to baseline | | −0.81% | 0.69% | 2.16% |
| % Difference to previous | | −0.81% | 1.49% | 1.48% |
| p-Value against Baseline | | 2.15E−01 | 4.31E−01 | 5.13E−02 |

TABLE 12

CHROMAMETER CR300 ® data for untreated areas of the skin of the subjects

| | Untreated | | | |
|---|---|---|---|---|
| | Baseline | Week 4 | Week 8 | Week 12 |
| Mean | 60.66 | 60.71 | 60.42 | 59.55 |
| % Difference to baseline | | −0.07% | 0.40% | 1.84% |
| % Difference to previous | | −0.07% | 0.47% | 1.45% |
| p-Value against Baseline | | 8.83E−01 | 5.23E−01 | 1.25E−02 |

CORNEOMETER® CM825 assessments were performed according to the methods described in Example 6. CORNEOMETER® CM825 values of skin moisturization at both the test site and untreated site show no statistically significant hydration under humectant property measurements (Tables 13 and 14). A mean rise in moisture content of the skin was observed however as this was observed for both the treated and untreated control sites no efficacious effect of the article can be considered valid.

TABLE 13

CORNEOMETER ® CM825 data for treated areas of the skin of the subjects

| | Treated | | | |
|---|---|---|---|---|
| | Baseline | Week 4 | Week 8 | Week 12 |
| Mean | 36.24 | 43.66 | 39.63 | 43.35 |
| % Difference to baseline | | 20.49% | 9.36% | 19.63% |
| % Difference to previous | | 20.49% | −9.24% | 9.39% |
| p-Value against Baseline | | 9.17E−02 | 2.29E−01 | 1.02E−01 |

TABLE 14

CORNEOMETER ® CM825 data for untreated areas of the skin of the subjects

| | Untreated | | | |
|---|---|---|---|---|
| | Baseline | Week 4 | Week 8 | Week 12 |
| Mean | 34.51 | 39.75 | 38.33 | 44.68 |
| % Difference to baseline | | 15.15% | 11.04% | 29.46% |
| % Difference to previous | | 15.15% | −3.57% | 16.59% |
| p-Value against Baseline | | 2.17E−01 | 1.39E−01 | 5.08E−04 |

Visual assessments were performed according to the methods described in Example 7. Visual assessments according to the Glogau scale of visible ageing (Table 5) showed a 34.51% reduction in the visible aging score observed for the treated site following 12 weeks of usage (Table 15). The untreated site showed no observable reduction in visible ageing following 12 weeks of usage (Table 15).

TABLE 15

Visual assessment data for treated and for untreated areas of the skin of the subjects

| | Treated | | | Untreated | | |
|---|---|---|---|---|---|---|
| | Baseline | Week 8 | Week 12 | Baseline | Week 8 | Week 12 |
| Mean | 3.09 | 2.09 | 2.02 | 3.09 | 3.09 | 3.15 |
| % Difference to baseline | | 32.27% | 34.51% | | −0.13% | −2.11% |
| % Difference to previous | | 32.27% | 3.31% | | −0.13% | −1.98% |

The test composition of Example 1, Table 1 showed excellent results in reducing wrinkles, increasing firmness of the skin, and increasing elasticity of the skin. The test composition of Example 1, Table 1 treated photoaging based on evaluation of the skin of the subject and observing the following effects anti-wrinkle; visible reduction of fine lines and wrinkle; reduction of the appearance of fine lines and wrinkles by about 9% in 12 weeks; skin firming; improvement of skin texture; improvement of skin elasticity by about 60% in 12 weeks; firming the skin by about 38% in 8 weeks.

Although the invention has been described with reference to the above examples, it will be understood that modifications and variations are encompassed within the spirit and scope of the invention.

What is claimed is:

1. A composition consisting of:
    a) a first anti-acne compound;
    b) a second anti-acne compound, wherein each of the first and second anti-acne compounds are selected from the group consisting of azelaic acid, clindamycin, niacinamide, and zinc pyrithione, or a pharmaceutically acceptable salt thereof;
    c) an anti-photoaging compound, wherein the anti-photoaging compound is selected from the group consisting of azelaic acid, and niacinamide, or a pharmaceutically acceptable salt thereof, and
    d) a pharmaceutically acceptable vehicle,
    wherein the first anti-acne compound, the second anti-acne compound, and the anti-photoaging compound are three different compounds.

2. The composition of claim 1, wherein the composition comprises clindamycin phosphate.

3. The composition of claim 1, wherein the composition comprises niacinamide.

4. The composition of claim 1, wherein the composition comprises azelaic acid.

5. The composition of claim 1, wherein the composition comprises clindamycin, zinc pyrithione, and niacinamide.

6. The composition of claim 1, wherein the composition comprises clindamycin, niacinamide, and azelaic acid.

7. The composition of claim 1, wherein the composition comprises clindamycin, zinc pyrithione, and azelaic acid.

8. The composition of claim 1, wherein the composition comprises niacinamide, zinc pyrithione, and azelaic acid.

9. A method for the treatment of acne and photoaging in a subject in need thereof comprising administering to the skin of the subject a composition consisting of:
    a) a first anti-acne compound;
    b) a second anti-acne compound, wherein each of the first and second anti-acne compounds are selected from the group consisting of azelaic acid, clindamycin, niacinamide, and zinc pyrithione, or a pharmaceutically acceptable salt thereof;
    c) an anti-photoaging compound, wherein the anti-photoaging compound is selected from the group consisting of azelaic acid, and niacinamide, or a pharmaceutically acceptable salt thereof; and
    d) a pharmaceutically acceptable vehicle,
    wherein the first anti-acne compound, the second anti-acne compound, and the anti-photoaging compound are three different compounds.

10. The method of claim 9, wherein the composition comprises clindamycin, zinc pyrithione, and niacinamide.

11. The method of claim 9, wherein the composition comprises clindamycin, niacinamide, and azelaic acid.

12. The method of claim 9, wherein the composition comprises clindamycin, zinc pyrithione, and azelaic acid.

13. The method of claim 9, wherein the second composition comprises niacinamide, zinc pyrithione, and azelaic acid.

14. A kit comprising:
    1) a composition consisting of
        a) a first anti-acne compound;
        b) a second anti-acne compound, wherein each of the first and second anti-acne compounds are selected from the group consisting of azelaic acid, clindamycin, niacinamide, and zinc pyrithione, or a pharmaceutically acceptable salt thereof;
        c) an anti-photoaging compound, wherein the anti-photoaging compound is selected from the group consisting of azelaic acid, and niacinamide, or a pharmaceutically acceptable salt thereof, and
        d) a pharmaceutically acceptable vehicle,
        wherein the first anti-acne compound, the second anti-acne compound, and the anti-photoaging compound are three different compounds; and
    2) a sealed container for housing the composition.

15. The kit of claim 14, wherein the composition comprises clindamycin, zinc pyrithione, and niacinamide.

16. The kit of claim 14, wherein the composition comprises clindamycin, niacinamide, and azelaic acid.

17. The kit of claim 14, wherein the composition comprises clindamycin, zinc pyrithione, and azelaic acid.

18. The kit of claim 14, wherein the composition comprises niacinamide, zinc pyrithione, and azelaic acid.

19. A composition comprising between 0.009% w/w and 0.15% w/w tretinoin, between 2% w/w and 6% w/w niacinamide and between 2% w/w and 8% w/w magnesium ascorbyl phosphate.

20. The composition of claim 19, comprising between 0.017% w/w and 0.1% w/w tretinoin, between 2% w/w and 6% w/w niacinamide and between 2% w/w and 8% w/w magnesium ascorbyl phosphate.

21. The composition of claim 20 comprising about 0.02% w/w tretinoin, about 4% w/w niacinamide and about 5% w/w magnesium ascorbyl phosphate.

22. A composition consisting of between 0.009% w/w and 0.15% w/w tretinoin, between 2% w/w and 6% w/w niacinamide and between 2% w/w, 8% w/w magnesium ascorbyl phosphate and a pharmaceutically acceptable vehicle.

23. The composition of claim 22, consisting of between 0.017% w/w and 0.1% w/w tretinoin, between 2% w/w and 6% w/w niacinamide and between 2% w/w, 8% w/w magnesium ascorbyl phosphate and a pharmaceutically acceptable vehicle.

24. The composition of claim 23 consisting of about 0.02% w/w tretinoin, about 4% w/w niacinamide and about 5% w/w magnesium ascorbyl phosphate and a pharmaceutically acceptable vehicle.

* * * * *